(12) United States Patent
Mehta (10) Patent No.: US 8,074,899 B2
(45) Date of Patent: Dec. 13, 2011

(54) AIRBRUSH MAKEUP APPLICATION SYSTEM AND METHODS OF USE

(75) Inventor: Pershant Mehta, Stafford, TX (US)

(73) Assignee: Luminess LP, Stafford, TX (US)

( * ) Notice: Subject to any disclaimer, the term of this patent is extended or adjusted under 35 U.S.C. 154(b) by 295 days.

(21) Appl. No.: 12/291,117

(22) Filed: Nov. 6, 2008

(65) Prior Publication Data

US 2009/0114236 A1    May 7, 2009

Related U.S. Application Data

(60) Provisional application No. 61/001,945, filed on Nov. 6, 2007.

(51) Int. Cl.
*B05B 7/30* (2006.01)
(52) U.S. Cl. ........................ 239/346; 239/345
(58) Field of Classification Search ................. 239/346, 239/310, 311, 318, 337, 345, 354, 379, 569, 239/581.2, 582.1, 8, 10, 11, 589, 592, 593, 239/596, DIG. 21
See application file for complete search history.

(56) References Cited

U.S. PATENT DOCUMENTS

| | | | |
|---|---|---|---|
| 4,187,058 A | 2/1980 | Fish | |
| 5,454,517 A * | 10/1995 | Naemura | 239/390 |
| 6,105,881 A * | 8/2000 | Kitajima | 239/353 |
| 6,213,131 B1 * | 4/2001 | Vien et al. | 132/285 |
| 2003/0071144 A1 | 4/2003 | Naemura | |
| 2005/0063915 A1 | 3/2005 | Halston | |
| 2005/0255062 A1 | 11/2005 | McKenna | |
| 2005/0263613 A1 | 12/2005 | Beck et al. | |

OTHER PUBLICATIONS

Blaine R. Copenheaver (authorized officer), International Searching Authority/United States, International Search Report, Mar. 3, 2009, 3 pages, PCT/U.S. Patent and Trademark Office, Alexandria, Virginia.
Blaine R. Copenheaver (authorized officer), International Searching Authority/United States, International Written Opinion of the International Searching Authority, Mar. 3, 2009, 6 pages, PCT/U.S. Patent and Trademark Office, Alexandria, Virginia.

\* cited by examiner

*Primary Examiner* — Davis Hwu
(74) *Attorney, Agent, or Firm* — Louis C. Paul & Assoc., PLLC (57) ABSTRACT

Make-up application systems are provided that comprise an air compressor unit, an airbrush connected to the air compressor unit, the airbrush having a gravity feed cup, and a tube connecting the air compressor unit to the airbrush. A cosmetic formulation comprising at least one mineral and water may be introduced into the gravity feed cup, which may then be aspirated into the airbrush and dispersed in a fine mist or atomized spray for delivery on a surface such as a person's skin. The system permits a more flawless make-up application finish for the face, neck and chest, and body, permitting feathering and blending not capable with traditional brush or sponge make-up application systems. Advantages are numerous and include, a more desirable appearance, longer lasting and quicker drying make-up, avoidance of harmful toxins and skin irritants, and enhanced hygienic application. Additionally, certain embodiments enjoy a quiet compressor operation through the use of isolation devices, certain materials of construction, and/or cushioning sponges.

7 Claims, 5 Drawing Sheets

AIRBRUSH MAKEUP APPLICATION SYSTEM AND METHODS OF USE

CROSS-REFERENCE TO RELATED APPLICATION

This patent application claims priority to and the benefit of U.S. Provisional Patent Application Ser. No. 61/001,945, entitled, "Airbrush Makeup Application System and Methods for Use," filed Nov. 6, 2007.

BACKGROUND

The present application relates to the field of cosmetics and the application thereof, and more particularly to a self-application airbrush makeup systems, cosmetic formulations for use therewith, and methods of use.

The cosmetic market has recently been estimated to be as large as $19 billion dollars. A subset of the cosmetic market, called "make-up" refers primarily to decorative cosmetics applied to one's skin to alter or complement its appearance. Conventional make-up generally consists of a powder, liquid, or gel substance that is applied directly to the skin via a sponge, brush, or other applicator.

Disadvantages of conventional make-up and their corresponding application techniques are numerous. Traditional makeup formulations, as well as other brush on formulations, are generally in powder form. Such powders are undesirable because they are dry, flakey, dusty and have a tendency to spread onto counters, vanities, and the like, creating undesired mess. Liquid makeup, on the other hand, is primarily silicone based or water based or alcohol based and can appear ashy or caked-on when applied. Conventional make-up often leaves a fake or non-natural "mask" appearance to one's face. The powder and liquid formulations can result in dry, flakey, dusty or cake-like build-ups of make-up, which can often further enhance undesirable features such as ridge lines that users wish to conceal. Additionally, conventional powders and liquids used for make-up often leave users with a non-natural feeling on their skin. These conventional formulations also fail to adhere well to the skin, resulting in smudged make-up or make-up that rubs off on to one's clothes, hands, cell phones, or other articles that come into contact with one's skin. Furthermore, conventional formulations, because of their dry, flakey, powder nature, have a tendency to spread onto counters, vanities, and the like, creating an undesired mess.

Moreover, conventional make-up typically only lasts for a limited duration, frequently needing to be reapplied. In other words, conventional make-up has a tendency to easily rub off over time.

Some decorative cosmetics are primarily oil based and hence, leave users with an undesirable oily feel or in some cases irritate or cause harm to a user's skin. Some decorative cosmetics contain toxic chemicals, preservatives, or otherwise harmful ingredients, especially those derived from petroleum, sodium lauryl sulfate (SLS), and parabens. Some surfactants such as SLS have been known to cause a number of skin conditions, including dermatitis. Other substances such as parabens can cause skin irritation and contact dermatitis in individuals with paraben allergies, a small percentage of the general population. Animal experiments have shown that parabens have a weak estrogenic activity, acting as xenoestrogens. Moreover, prolonged use of this type of prior art makeup has also been linked to thinning eyelashes.

Not only do conventional decorative cosmetics often contain harmful components, they often fail to include substances for treating or enhancing the healthiness of one's skin. By not including ingredients that further promote or enhance healthy skin, users may be forced to apply these substances separately. In the case of such substances being applied over make-up, the substances may lose their effectiveness and cause the underlying make-up to smear, smudge or otherwise alter the desired result. In the case of such substances being applied before make-up application, the applied make-up may cake up or fail to adhere to the skin.

Another disadvantage of conventional decorative cosmetics derives from its mode of application. As mentioned above, the most popular methods of applying conventional cosmetics are by way of sponges, brushes, or other applicator devices. Reusing such applicators can promote the build-up or spreading of dirt, bacteria, or grime. Thus, not only to avoid the accumulation of grime and dirt, but also for hygienic reasons, it is desirable to avoid reusing an applicator to apply decorative cosmetics.

SUMMARY

The present application relates to the field of cosmetics and the application thereof, and more particularly to airbrush makeup application systems, cosmetic formulations for use therewith, and methods of use.

One example of a make-up application system comprises an air compressor unit having an compressor outlet port; an airbrush stylus comprising an air inlet port, an air outlet port, and a flowpath from the air inlet port to the air outlet port wherein the flowpath comprises a flow restriction; a gravity feed cup in communication with the flowpath adjacent to the flow restriction; a tube connecting the compressor outlet port of the air compressor unit to the air inlet port of the airbrush; a cosmetic formulation comprising at least one mineral and water adapted to be aspirated into the airbrush via the gravity feed cup; and a variable throttle valve configured to modulate the flow of the cosmetic formulation from the gravity feed cup into the airbrush.

One example of a method for applying a decorative cosmetic comprises the steps of: providing a make-up application system comprising an air compressor unit having an air outlet port, an airbrush having a gravity feed cup thereon and an air inlet port, a tube connecting the air outlet port of the air compressor unit to the air inlet port of the airbrush, and a cosmetic formulation comprising at least one mineral and water adapted to be aspirated into the airbrush via the gravity feed cup; introducing the cosmetic formulation into the gravity feed cup; activating the air compressor unit; allowing the cosmetic formulation to be aspirated into the airbrush; and allowing the cosmetic formation to be dispersed in a directed atomized spray out the air outlet port onto a surface.

One example of a make-up application system comprises an air compressor unit having an air outlet port; an airbrush having a gravity feed cup thereon and an air inlet port; a tube connecting the air outlet port of the air compressor unit to the air inlet port of the airbrush; and a cosmetic formulation comprising at least one mineral and water adapted to be aspirated into the airbrush via the gravity feed cup.

One example of a method for applying a matching makeup formulation to the skin, said method comprising the steps of: providing at least two color shades in each of four color groups; applying each color to the skin; determining if one of the two colors matches the skin; if one of the two colors matches the skin, charging an airbrush with the matching color and applying the color to the skin; and if neither of the two colors matches the skin, charging an airbrush with both colors, mixing the colors in the airbrush and applying the mixed colors to the skin.

One example of a make-up application kit for permitting home consumers to apply airbrush cosmetic formulations utilizing a miniaturized, portable airbrush application system comprises an air compressor unit having an compressor outlet port; an airbrush stylus comprising an air inlet port, an air outlet port, and a flowpath from the air inlet port to the air outlet port, said airbrush stylus having a single action trigger to cause makeup and air to flow through the stylus and a gravity feed cup in communication with the flowpath between said air inlet port and air outlet port; a tube connecting the compressor outlet port of the air compressor unit to the air inlet port of the airbrush; and a cosmetic formulation comprising at least one mineral and water adapted to be aspirated into the airbrush via the gravity feed cup.

The features and advantages of the present invention will be apparent to those skilled in the art. While numerous changes may be made by those skilled in the art, such changes are within the spirit of the invention.

BRIEF DESCRIPTION OF THE DRAWINGS

A more complete understanding of the present disclosure and advantages thereof may be acquired by referring to the following description taken in conjunction with the accompanying figures, wherein.

While the present invention is susceptible to various modifications and alternative forms, specific exemplary embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DESCRIPTION OF PREFERRED EMBODIMENTS

The application claims priority to U.S. Patent Application Ser. No. 61/001,945 filed on Nov. 6, 2007

The present application relates to the field of cosmetics and the application thereof, and more particularly to airbrush makeup application systems, cosmetic formulations for use therewith, and methods of use. Particularly, the system of the present invention is provided to permit home consumers to self-apply the unique cosmetic formulations of the invention utilizing air-brush application.

In certain embodiments, make-up application systems of the present invention comprises a small, compact, miniaturized air compressor unit, an airbrush stylus connected to the air compressor unit, the airbrush stylus having a gravity feed cup thereon, a tube connecting the air compressor unit to the airbrush stylus and a cosmetic formulation comprising at least one mineral and water for introduction into the gravity feed cup. The cosmetic formulation may then be aspirated into the airbrush stylus and dispersed in a fine mist or atomized spray for delivery on a person's skin.

Advantages of certain embodiments are numerous and include, but are not limited to, the ability to self-apply airbrush make-up, a more desirable make-up appearance, longer lasting make-up, quicker drying cosmetic formulations, faster application times compared to traditional sponge/brush application, avoidance of harmful toxins or skin irritants, and enhanced hygienic application of decorative cosmetics. Additionally, certain embodiments enjoy a quiet compressor operation through one or more of the following: isolation devices, certain materials of construction, and cushioning sponges. Moreover, the atomized spray from certain embodiments of the device have a desirable cooling and therefore relaxing effect on the user. The system permits a more flawless make-up application finish for the face, neck and chest, and body permitting feathering and blending not capable with traditional brush or sponge make-up application systems. These advantages and others are explained in more detail throughout the specification.

To facilitate a better understanding of the present invention, the following examples of certain embodiments are given. In no way should the following examples be read to limit, or define, the scope of the invention.

Figure 1:
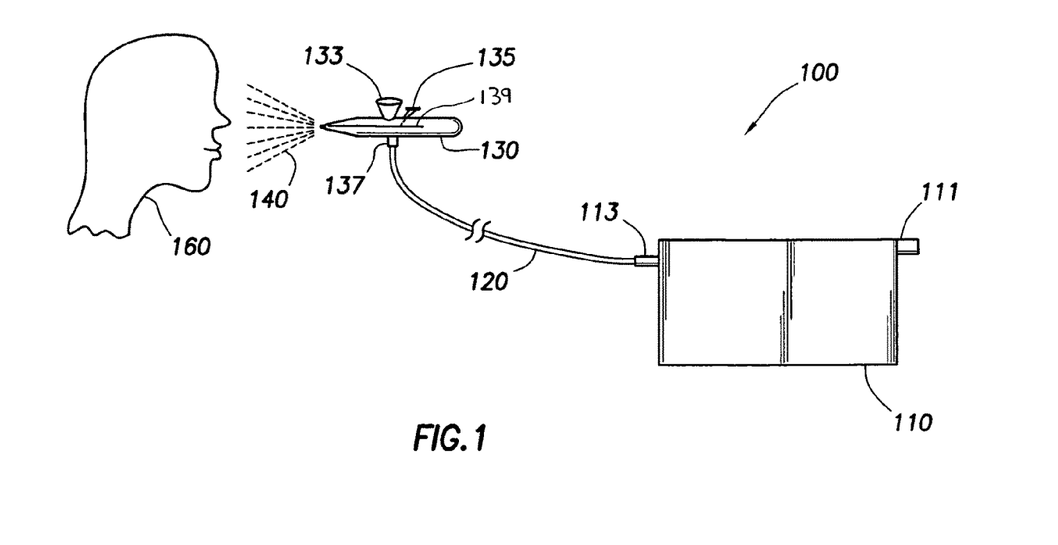
FIG. 1 illustrates a schematic view of a make-up application system in accordance with one embodiment of the present invention.

FIG. 1 illustrates a schematic view of a make-up application system in accordance with one embodiment of the present invention. Certain embodiments of make-up application system 100 generally comprise a small, compact, miniaturized air compressor unit, an airbrush stylus, and a tube connecting the air compressor unit to the airbrush stylus. Although each of these components are disclosed in greater detail throughout the specification, a broad overview is shown in FIG. 1. Generally, air compressor unit 110 draws in air from air compressor inlet port 111 and discharges air through air compressor outlet port 113. The stream of air flows through tube 120 to airbrush stylus 130. The compressed air enters airbrush stylus 130 at air inlet port 137. The compressed air follows an air path in airbrush stylus 130 and aspirates in a portion of the cosmetic formulation that is charged in gravity feed cup 133. The cosmetic formulation from gravity feed cup 133 forms an atomized mist and a finely dispersed spray 140 onto a person's skin 160, for example, a portion of a person's face.

Variable throttle 135 adjusts the quantity of cosmetic formulation that is aspirated into airbrush stylus 130 to control the flow rate cosmetic formulation dispersed from airbrush stylus 130 so as to provide a lighter or heavier application, as desired. Specifically, throttle 135 is attached to needle 139 provided along the elongated axis of airbrush stylus 130. When throttle 135 is in a first closed position, a portion of the axial needle seats in opening or aperture through which the make-up formulation is ejected from the stylus, so as to inhibit the flow of compressed air through the airbrush stylus. When the throttle 135 is moved to a second open position, the axial needle is removed from the opening, so as to permit air to flow through the airbrush stylus. Intermediate positions of throttle 135 between fully open and fully closed permit more precise control of make-up flow from the airbrush stylus.

Although gravity feed cup 133 is depicted herein as a top-loading airbrush, it is explicitly recognized that a bottom-feed airbrush (or a combination bottom-feed and gravity-feed airbrush) could be used in the system, particularly where larger quantities of makeup or tanning solution for large coverage area, like the body.

Alternative embodiments of airbrush stylus 130 comprise a removable tip to allow for easier cleaning of airbrush stylus. The flowpath in airbrush stylus comprises a removable needle in some embodiments also to allow easier cleaning. Methods of cleaning of the airbrush stylus include flushing the device with a solvent such as water or alcohol. When desired, the solvent may be introduced into the gravity feed cup and the air compressor activated so as to flush out the airbrush stylus. In this way, the airbrush stylus is kept clean, has reduced risk of plugging, and promotes good hygienic practices. In this way, the build-up of bacteria and germs that is typical of conventional sponge make-up applicators is avoided.

Figure 2:
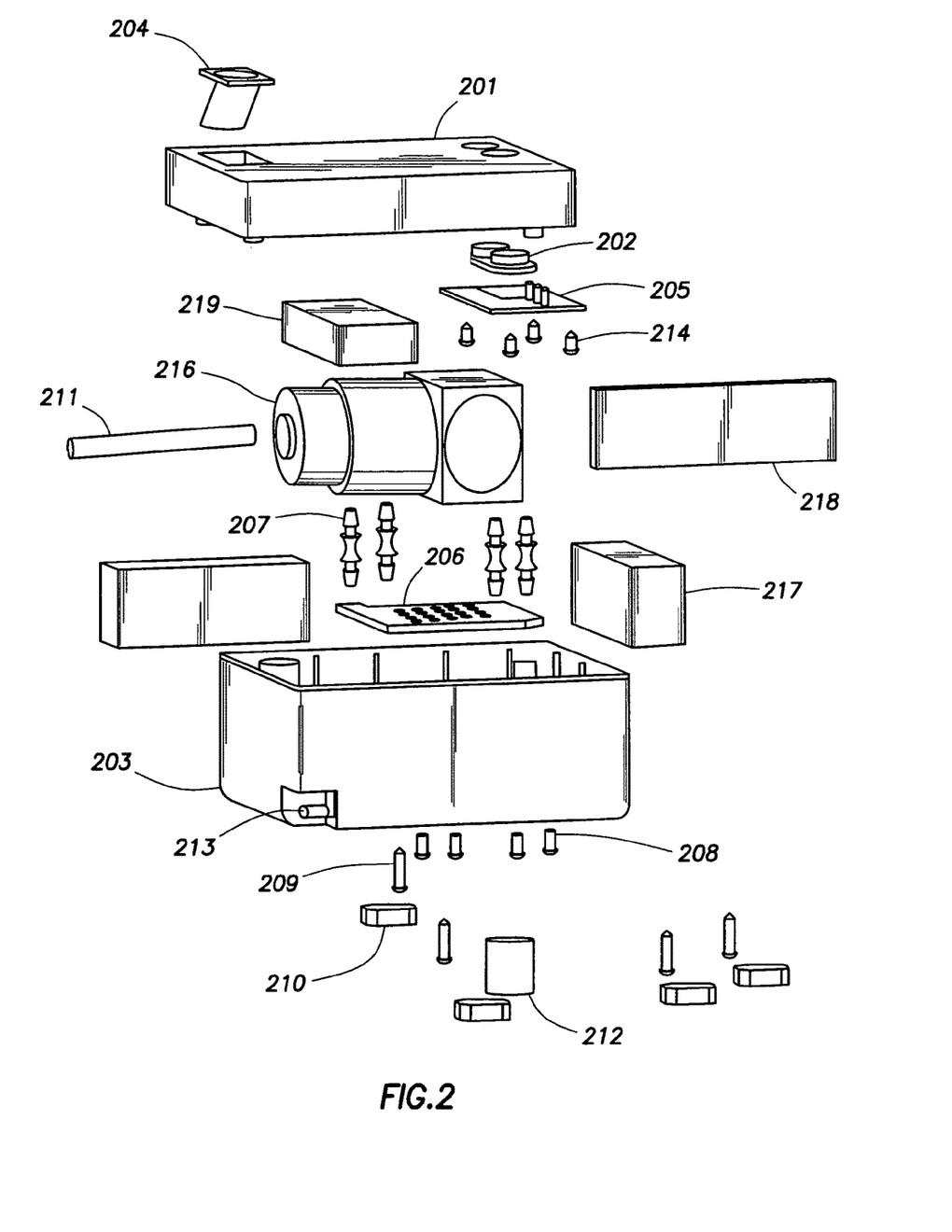
FIG. 2 illustrates an exploded view of an air compressor unit of a make-up application system in accordance with one embodiment of the present invention.

One unique aspect of the system of the invention is the small, compact, miniaturized air compressor unit 200 which is shown in FIG. 2. In one embodiment, air compressor unit 200 is approximately 100 mm wide, by 125 mm long by 55 mm tall. In another embodiment, the air compressor unit is approximately 115 mm long by 80 mm wide by 58 mm tall. More specifically, as shown in FIG. 2, air compressor 216 resides in an enclosed compartment comprised of upper cover 201 and base enclosure 203. Such compartment preferably has the dimensions described above, and as such, is easily transported and usable by home consumers.

In order to achieve the small size of the air compressor unit, a low-PSI air compressor 216 was utilized. While the low-PSI compressor 216 of the invention is highly suitable for delivering a cosmetic formulation as described herein, the smaller compressor permits the overall system to be miniaturized to the dimensions set forth above, so as to enhance the transportability and desirability of the system for home consumers. In certain embodiments, the system is of a one-touch button operation 202 to activate air compressor 216, and provides an air stream of a constant pressure, most desirably in the range of about 0.5 psi to about 20 psi, and preferably at 3-5 psi. Significantly, while the low-PSI permits a smaller air compressor to be incorporated into unit 200, so as to permit miniaturization, the low-PSI air compressor is also more desirable for the intended use of the invention, namely self-application of make-up by home consumers. The system is intended to permit home consumers to apply air brush make up to themselves. In this regard, it is anticipated that such consumers will hold the airbrush stylus in close proximity to the face and hence, a lower pressure output is desired for a more gentle application of make-up. In addition, a lower pressure output is easier to manipulate hence making it more desirable. Finally, a pressure setting of no more than 12 psi functions as a safety feature. Since a user is self-applying the make-up and is likely to hold the airbrush stylus close to the face and eyes, it is desirable to have a maximum limit on the pressure at which the make-up is delivered from the airbrush stylus.

Those skilled in the art will appreciate that such a compressor system is much small than compressors systems commonly found in industrial applications, garages, workshops and the like. In order to achieve the small size set forth above and provide a system capable of use by consumers for make-up self-application, a smaller compressor was utilized.

In another embodiment, the air stream can be adjusted between two or more different pressure levels. In yet another embodiment, 3-speed pre-sets are provided for light, medium and high air speeds so that one can perform the most delicate and/or sheer makeup of some areas, such as eye-brows, while permitting the system to also be used for larger areas where a heavier application may be desired, such as makeup applied to the legs, body, etc. Other embodiments include a variable turn dial for variably adjusting the compressor speed as desired. Still yet other embodiments include a single switch for operation, wherein depression of the switch a first time turns the compressor on and subsequent depressions of the switch allow a user to cycle through differing air pressure settings. Air straw 211 (also referred to as the air compressor inlet port) is provided for drawing in air to air compressor 216. Air outlet port 213 is also shown.

To further provide a product that is desirable by home consumers, air compressor unit 200 incorporates a number of features that provide for a quieter operation of air compressor 216. Soundproofing may be disposed within the compressor system case to minimize noise. For example, cushion sponges 212, 217, 218, and 219 add additional soundproofing through absorption of noise and dampening of vibrations.

Additionally, the system includes a compressor isolation mounting to minimize vibrations of the system and soundproofing to minimize system noise during operation. Air compressor 216 is mounted on isolation platform 206 or cushion, which is itself suspended on one or more isolation legs 207. Preferably, isolation platform 206 and/or isolation legs 207 are elastomeric to further reduce vibration transfer. In one embodiment, four elastomeric legs 207 are compressed or otherwise secured between a top and bottom of the enclosed compartment 203 and isolation platform 206 "floats" in a concave contour on each leg 207. Not only does this further reduce vibrations, it also simplifies manufacture. In another embodiment, isolation platform 206 rides on shoulders on isolation legs 207. Screws 208, 209, and 214 are used to attach the various components although any attachment mechanism known in the art may be used.

Base grips 210 provide additional isolation from compressor vibration and allow further dampening of any noise. Additionally, base grips 210 reduces slippage of air compressor unit 300.

Airbrush holder 204 may be incorporated into air compressor unit 200 for providing a receptacle for receiving an airbrush stylus when the airbrush stylus is not in use. Printed circuit board (PCB) 205 provides the electronics necessary for operation of air compressor unit 200.

As will be described in more detail below, the airbrush stylus preferably has a gravity feed cup mounted thereon into which make-up can be charged. Since the gravity feed cup is located on the top of the airbrush stylus and easily accessible, the system permits one to readily change between types of makeup—foundation/base, blush, bronzing, body shimmer, highlighter, etc.—or between colors thereof. The airbrush stylus also can quickly be flushed with water or other liquid for use with other colors of makeup types. Of course, a bottom feed airbrush (or a combination bottom feed and gravity feed airbrush) can also be used in the system in the event larger quantities of makeup or tanning solution for large coverage area like the body.

In another embodiment of the invention, the airbrush stylus includes a single action mechanism for operation of the airbrush stylus, where the actuation of a single "trigger" results in paint and air flowing into the airbrush body and the atomized paint being expelled onto the target surface. A single action airbrush stylus is preferable because of the ease of use by consumers. The trigger action may be a push action, a pull action or depression action so long as a single action results in paint and air flow. In contrast, a dual action or double action airbrush stylus separates the function for air and paint flow so that the user can control the volume of airflow and the concentration of paint flow through two independent mechanisms. This allows for greater control and a wider variety of artistic effects, but has been determined to be more difficult for home consumers to manipulate and utilize.

Those skilled in the art will appreciate that for purposes of the invention and based on the intended use of the invention, namely makeup application by consumers, an internal mix airbrush stylus is preferred and described, wherein the paint and air mixes inside the airbrush (in the tip) creating a finer atomized "mist" of paint.

Figure 3A:
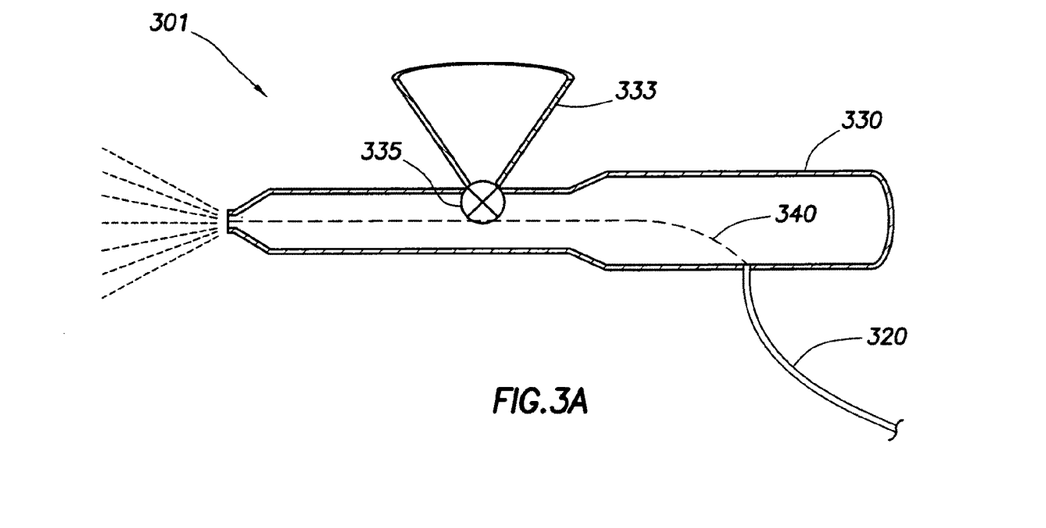
FIGS. 3A-3D illustrate cross-sectional views of an airbrush flowpath in accordance with one embodiment of the present invention.

FIGS. 3A-3D illustrate cross-sectional views of an airbrush stylus flowpath in accordance with various embodiments of the present invention. Although any type of flow restriction may be used to generate the aspiration effect so as to generate a finely dispersed mist or spray via the venture principle. FIGS. 3A-3D show several suitable embodiments for accomplishing the necessary aspiration. More specifically, FIG. 3A shows airbrush stylus 301 having a restriction in its flowpath 340 formed by a truncated cone in airbrush stylus 330. Variable throttle 335, shown schematically here, may be used to adjust the flow of cosmetic formulation that aspirates into airbrush stylus 330.

Figure 3B:
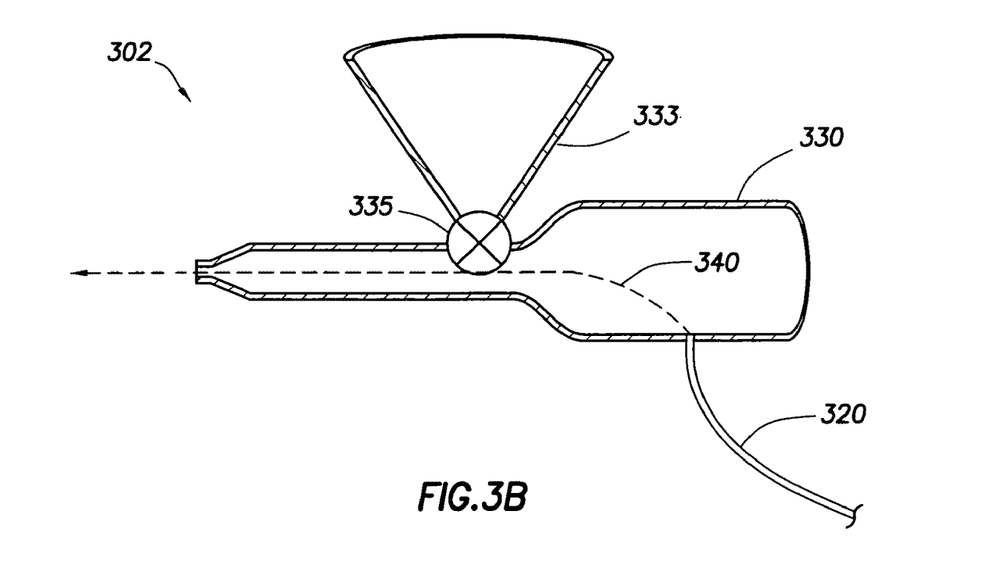
Figure 3C:
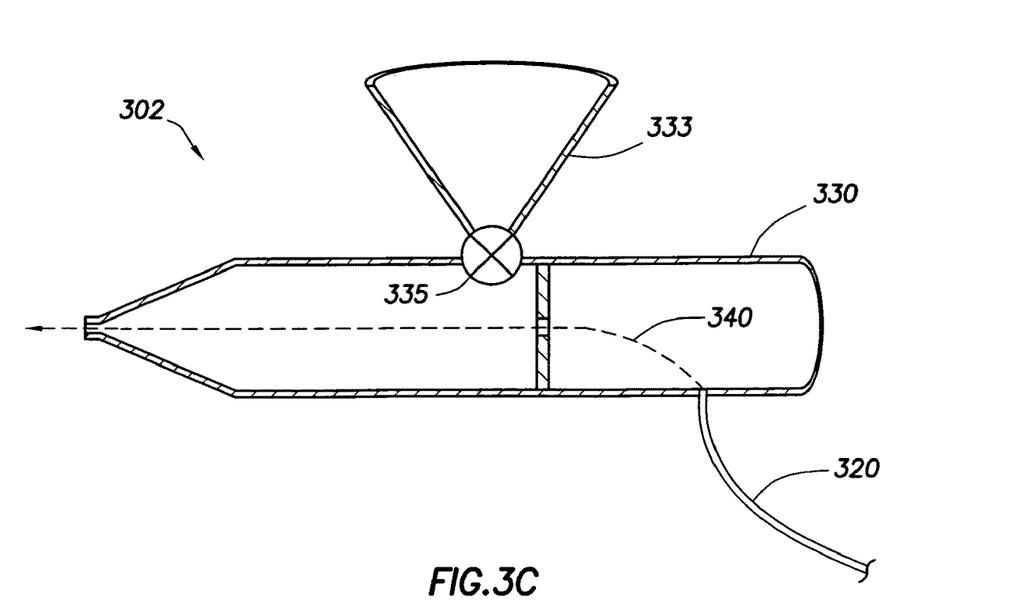

FIG. 3B shows an example of a convergent/divergent nozzle configuration, whereas FIG. 3C shows an orifice plate used to accomplish a similar effect.

Figure 3D:
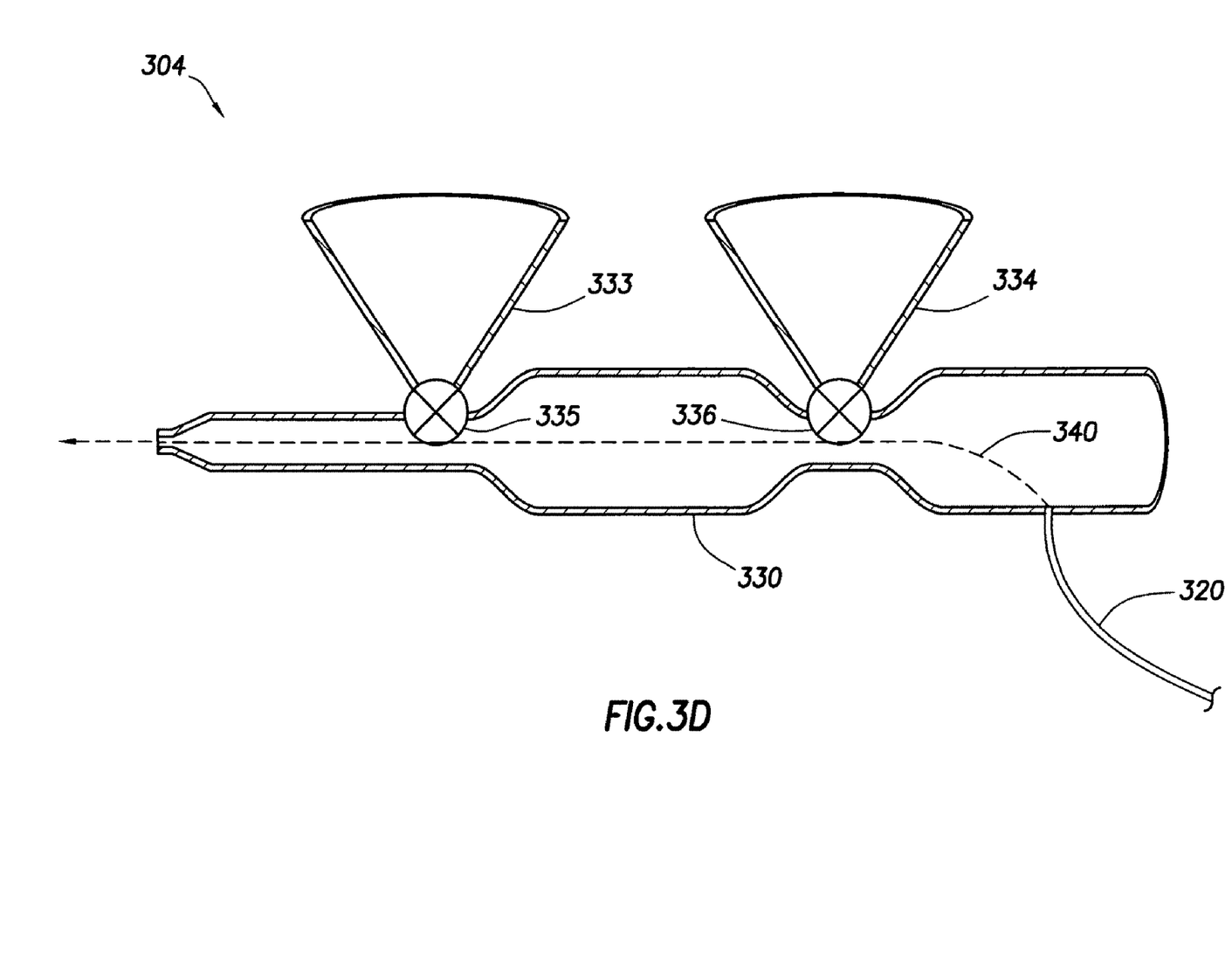

FIG. 3D shows multiple staged gravity feed cups being used. In this configuration, each gravity cup 333 and 334 may be charged with the same cosmetic formulation or different cosmetic formulations, including different shades of cosmetic formulations as desired.

In one preferred embodiment, a 35 mm tip is utilized for ejection of the makeup from the airbrush stylus.

Make-Up Formulations

To operate with the lower PSI of such a small compressor and to readily pass through the small orifice within the airbrush stylus, it was necessary to develop a make-up formulation comprised significantly of water, so as to permit the formulation, when charged in the cup of the airbrush, to easily and smoothly flow through the airbrush without clogging the airbrush stylus. It will be appreciated that traditional liquid cosmetic formulations (such as silicone-based formulations) and those other formulations of the prior art (such as powder or other dry formulations) would readily clog or plug up the feed cup and small orifices and annulus of the airbrush stylus of the invention, so as to frustrate the application of make-up, and particularly, the smooth application achievable with the invention.

Moreover, the cosmetic formulations incorporate hydrated minerals for coloration. One desirable feature of the current system is that is capitalizes on the beneficial traits of mineral based make-up, but avoids the drawbacks by hydrating the minerals in water. Heretofore, no one has created water based, mineral makeup formulations for airbrush application as is contemplated by the invention.

Specifically, the formulations utilize crushed minerals from the earth as the primary component other than water, and may be free of other chemical ingredients, preservatives, fillers, binders, oil, fragrance, talc and other skin irritants that can be harmful to the skin. In one preferred embodiment, formulations are made only from the following five mineral ingredients: titanium dioxide, zinc oxide, mica, iron oxide, bismuth oxychloride. Any combination thereof may be used as well.

Suitable formulations comprise hydrated minerals having at least about 50% water. Other suitable embodiments comprise at least about 60% water, from about 50% to about 99.8% water, or at least about 95% water. The most preferred embodiment of the invention comprises 70-80% by weight of water and 8-15% by weight of hydrated minerals. Significantly, being water based, the formulations are "interloceable," so as to permit various base formulations of the invention (such as foundation, blush, shippers, hair colors, sun screens, moisturizers, etc.) to be sprayed or otherwise applied together, regardless of shade.

In another embodiment of the invention, naturally occurring olive oil based ingredient may be added to the formulation. Olive oil is an excellent source of antioxidant polyphenols and vitamin E. Polyphenols are naturally occurring molecules in plants that are extremely gentle, efficient, and multi-faceted antioxidants. They are exceptionally stable and protective and accordingly, beneficial to both health and longevity. A powerful member of the olive oil polyphenol group is hydroxytyrosol. Extremely rare and effective in even small concentrations, this super antioxidant has been proven to be effective in enhancing the appearance of healthy skin. When used topically, it causes skin to appear smooth and more radiant and is thus a desirable ingredient in one embodiment of the invention.

Each of these components may be incorporated into the cosmetic formulations or added as a separately applied layer to the skin. Alternatively, these components may be charged into the gravity feed cup along with the cosmetic formulation. Being that the formulations are interloceable, these components will readily mix in the airbrush stylus as they are drawn through the stylus for application to one's skin.

Likewise, a humectant may also be desirable as an ingredient of the cosmetic formulations. A humectant is a hygroscopic substance. It is often a molecule with several hydrophilic groups, most often hydroxyl groups, but amines and carboxyl groups, sometimes esterified, can be encountered as well. The affinity to form hydrogen bonds with molecules of water is crucial and because of the significant amount of water in the foregoing formulations, highly desirable. Hygroscopic substances absorb water from the air and can keep the surface of the skin moist so as to provide moisturization of the skin.

Carrying Case

Figure 4A:
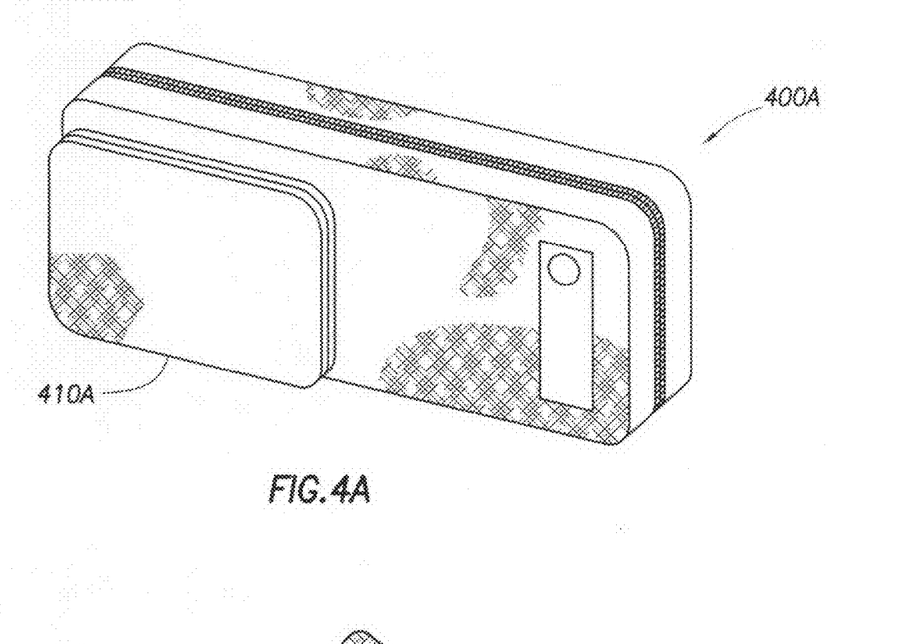
FIGS. 4A-4B illustrates a carrying and storage case for the airbrush application system of the invention.
Figure 4B:
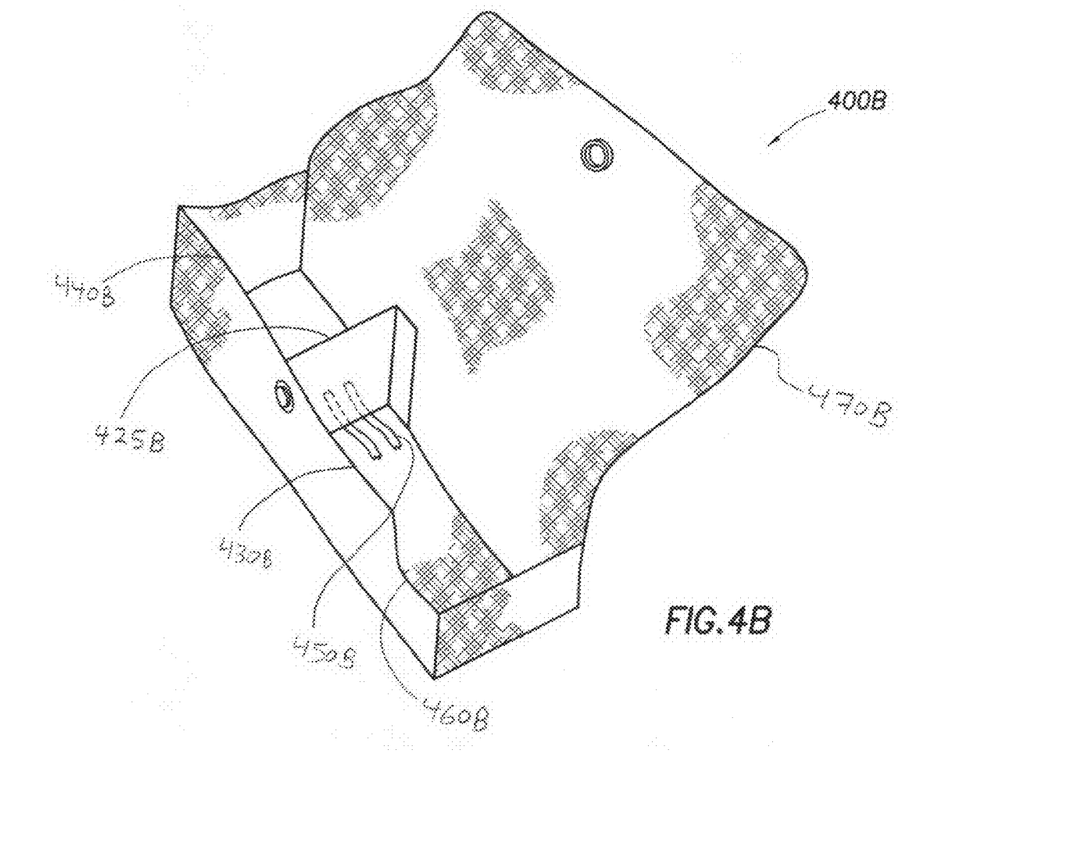

As shown in FIGS. 4A-4B, a uniquely designed carrying case for transport and use of the airbrush makeup application system is also provided. Turning to FIG. 4A, case 400A includes a main compartment into which the air compressor system can be inserted. A power pack may also be carried in the main compartment. Secondary compartment 410A is a smaller compartment on the exterior of case 400A houses the airbrush stylus. Disposed in the wall between the main compartment and secondary compartment 410a is an aperture to allow the airbrush hose to pass therethrough. Thus, the airbrush can be utilized without the need to remove the entire system from the case. A second compartment within the main compartment may be provided for storing make-up. In the preferred embodiment, the main compartment includes a window. Preferably, the window is formed of clear plastic and/or includes an opening adjacent the controls of the air compressor system. The air compressor system is disposed in the main compartment so that the window is adjacent the control features of the air compressor system. Thus, the air compressor system can be actuated and/or controlled without the need to remove it from the case. A shoulder strap, handle or similar feature can be included to permit easy carrying of the case.

In another embodiment shown in FIG. 4B, case 400B comprises two interior compartments 430B and 440B with wall 425B disposed therebetween. The air compressor system may be seated in first compartment 430B while the airbrush stylus may be carried in second compartment 440B. An aperture or opening in wall 425B between compartments 430B and 440B permits air hose 450B and other optional wires to pass therethrough. An opening or cutaway 460B in the exterior wall adjacent the controls of the air compressor system is provided to permit operation of the unit without removal of the air compressor unit from case 400B. The case includes fold-over top 470B, that when in the closed position, shields the air compressor from view so that case 400B has the appearance of an ordinary purse.

Methods

Make-up application systems of the present invention may be used in numerous ways. In certain embodiments, methods of use contemplate charging the gravity feed cup with a cosmetic formulation, which may be then aspirated into the airbrush stylus for application to a surface such as a person's skin. Two or more cosmetic formulations may be simultaneously charged in the gravity feed cup where blending of two formulations is desired (e.g. where blending of two shades of make-up is desired).

In certain embodiments, the surface or skin to be treated is first prepared with a pre-treatment substance. For example, a mattifying formulation or a moisturizing formulation may be applied directly to the skin before application of the cosmetic formulation. The mattifying or moisturizing formulations may be applied manually or via the make-up application system. Alternatively or additionally, other formulations may be applied after application of the cosmetic formulation or before application of the cosmetic formulation, including shimmering formulations, bronzing formulations, tanning formulations, blush, highlighter, foundation, base, or any other formulation in the art for enhancing one's appearance or physical health or condition. Multiple layers of each component may be applied as desired as well.

In certain preferred methods, the airbrush stylus is held approximately 4 to approximately 8 inches from the surface to be treated and the airbrush stylus is then moved in a flowing, circular motion so as to apply a sheer layer of formulation to the surface or skin. Typically, it is preferred to not hold the stylus in any one place, instead being preferable to keep the stylus constantly in a flowing motion to ensure an even uniform sheer layer of formulation to the area of application. A sheer effect is achieved through the application of a thin layer of the cosmetic formulation, which avoids the appearance of a fake make-up mask typical of conventional cosmetics. In this way, a person's appearance can be enhanced and appear to have a "natural glow."

Where specific areas such as blemishes, pimples, veins, and/or discolorations are desired to be treated, the airbrush stylus may be held closer to the skin. In certain embodiments, a lighter shade is used for close-up treatment for concealment of specific features. Then, the entire area may be treated with the desired finishing shade of make-up. Additionally, because the make-up application systems disclosed herein allow for such sheer layers of cosmetic formulations, the application of make-up herein allows for an enhanced concealment of certain features such as blemishes, veins, or ridges. In this way, the sheer layers conceal rather than enhance undesirable features as is the tendency with conventional make-up that has a tendency to enhance undesirable on account of build-ups of powder or liquid make-up.

An additional aspect of the system is a color selection process permitted by the system. Traditionally, a makeup foundation or base color is selected from one of four shades: fair, medium, tan or dark.

Typically, "fair" makeup is for the porcelain-light to fair skin color ranges. Such skin may have pale to rosy undertones. Such skin may freckle or burn easily under the sun and is typically more sensitive. "Medium" is probably the most common range for most women in the United States. Such skin has more natural undertones and tans well. Such skin may have pinkness with occasional surface redness or honey colorations. "Tan" skin has warmer to more olive undertones with exotic colorations which tan easily. Tan makeup colors are preferable for darker than average skin colors, such as slightly darker Latina, Mediterranean and East Indian skin colorations. Finally, "dark" color is best for those deeper caramel to coco color ranges with either golden or richer dusky colorations and is preferable for women of color ranging from the African American to the darker Latin American hues.

In any event, each of the four shades most commonly may have two colors associated with it. A user may select the shade and color closest to their skin color, which many consider the most "desirable" make-up color for the individual. Alternatively, one might try and "mix" colors by applying first one and then the other to the skin in multiple steps or layers. Notably, this "mixing" or blending occurs on the medium, i.e., the applicant's skin, by rubbing or brushing. Of course, once the foundation color is applied, in the prior art, additional application steps are required for bronzing, body shimmer and the like. These many steps are time consuming and hence, usually undesirable. As described below, the system of the invention allows color mixing and mixing of types of makeup in a single step. Traditional mixing happens in either of the three ways: Mixing one color then the next on the face, placing more than one color on a brush/applicator sponge then spread and mixed on the face or mixing more than one shade on a remote location like a dish or a surface and then application to the face or body.

The unique color selection system of the invention permits one to more closely match the exact skin color of the applicant. In each color group, at least two different shades of color are provided. In one preferred embodiment, three shades of color are provided within each group and in another preferred embodiment, four shades of color are provided within each color group. Preferably, the multiple shades within each color group have a progressively darker hue. Because the system is liquid based, a user can apply multiple shades to the skin and decide which shade or two shades are closest to skin color. If one color is an exact match, this color can be charged into the airbrush cup. In most instances, the best match will be in-between the two colors. Thus, one can charge the airbrush cup with a drop of each color. The colors thoroughly mix in the airbrush cup and passing through the airbrush stylus before the mixture ever reaches the applicant's skin. In other words, mixing occurs before application to the skin, unlike the prior art. As the airbrush atomizes the liquid makeup, the atomized drops of color are readily mixed together. This permits a much more homogonous application of the make-up. This system also permits much more precise mixing of colors to achieve the desired results. For example, one might elect to mix 3 parts of a first shade with 2 parts of a second shade. This blending is easily accomplished by charging the cup with three drops of the first shade and 2 drops of the second shade. Any other proportion or relative amounts of two or more cosmetic formulations may be blended in this way.

While the color selection system is possible with two or three colors in each shade, in the most preferred embodiment, four colors are provided in each of the above-referenced four color groups or skin shades. To "match" the best color, one applies a small amount of each of the four colors from the preferred shade to the skin. The two colors that most closely match the applicant's skin are charged into the airbrush cup. The colors may be provided in containers, each with a dropper so that the make-up can be dispensed in drops. It has been found that only a few drops of make-up are necessary for a single application. In any event, the droppers permit a more precise dispensing of the make-up from their respective containers, thus permitting the volumes to be mixed as desired. For example, two drops of each of the two closes colors may be charged into the cup. Alternatively, one can adjust the relative dispensed volumes to permit finer adjustment of the applied color mix. In this way, an almost exact match of skin color and foundation can be achieved, so as to accomplish the desired results of the invention.

The system as herein described is preferably provided in a kit comprising the compressor, the airbrush stylus, a tube for delivering air from the compressor to the stylus, at least two and preferably three or four shades from a select color group and a carrying case into which all of the foregoing components may be inserted, thereby providing a consumer product that is readily transportable and easily accessible for use.

The system as herein described permits a much more flawless make-up application finish for the face, neck and chest, and body by permitting feathering and blending not capable with traditional brush or sponge make-up application systems. Another desirable feature of the makeup application system of the invention is that it is hygienically more desirable. Unlike brushes and sponges that can easily become bacteria filled, the airbrush is made of materials that are easily cleaned and do not promote the growth of bacteria. Finally, the size and operating parameters if the system permit home consumers to easily transport and manipulate the system for self-application of make-up.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

What is claimed is:

1. A make-up application system comprising:
   an air compressor unit having an compressor outlet port;
   an airbrush stylus comprising an air inlet port, an air outlet port, and a flowpath from the air inlet port to the air outlet port wherein the flowpath comprises a flow restriction;
   a gravity feed cup in communication with the flowpath adjacent to the flow restriction;
   a tube connecting the compressor outlet port of the air compressor unit to the air inlet port of the airbrush;
   a cosmetic formulation comprising at least one mineral and water adapted to be aspirated into the airbrush via the gravity feed cup; and
   a variable throttle valve configured to modulate the flow of the cosmetic formulation from the gravity feed cup into the airbrush,
   wherein the air compressor unit comprises a base and a top disposed on the base so as to form an enclosed compartment, a suspension system disposed in the enclosed compartment, and a compressor attached to the suspension system wherein the compressor is in communication with the compressor outlet port;
   wherein the suspension system comprises at least one isolation leg secured within the enclosed compartment and a mounting platform attached to the at least one isolation leg, wherein the compressor is attached to the mounting platform so as to be suspended in the compartment;
   wherein the make-up application system comprises at least one base grip disposed on said base;
   wherein the isolation legs are elastomeric; and
   wherein the air compressor unit has a length no larger than 130 mm and a width no larger than 105 mm and a height no larger than 80 mm.

2. The make-up application system of claim 1 further comprising an airbrush holder secured to the top, wherein the air compressor has at least two preset PSI settings, wherein each preset PSI setting results in a different flowrate through the flowpath, wherein the cosmetic formulation comprises a plurality of micro-ground pigments.

3. A method for applying a decorative cosmetic comprising the steps of:
   providing a make-up application system comprising an air compressor unit having an air outlet port, an airbrush having a gravity feed cup thereon and an air inlet port, a tube connecting the air outlet port of the air compressor unit to the air inlet port of the airbrush, and a cosmetic formulation comprising at least one mineral and water adapted to be aspirated into the airbrush via the gravity feed cup;
   introducing the cosmetic formulation into the gravity feed cup;
   activating the air compressor unit;
   allowing the cosmetic formulation to be aspirated into the airbrush; and
   allowing the cosmetic formation to be dispersed in a directed atomized spray out the air outlet port onto a surface;
   providing a variable throttle valve configured to modulate the flow of the cosmetic formulation from the gravity feed cup into the airbrush wherein the cosmetic formulation comprises between about 50% and about 99.8% water;
   wherein the air compressor unit comprises a base and a top disposed on the base so as to form an enclosed compartment, a suspension system disposed in the enclosed compartment, and a compressor attached to the suspension system wherein the compressor is in communication with the compressor outlet port;
   wherein the suspension system comprises at least one isolation leg secured within the enclosed compartment and a mounting platform attached to the at least one isolation leg, wherein the compressor is attached to the mounting platform so as to be suspended in the compartment;
   wherein the make-up application system comprises at one base grip disposed on said base;
   wherein the isolation legs are elastomeric; and
   wherein the air compressor unit has a length no larger than 130 mm and a width no larger than 105 mm and a height no larger than 80 mm.

4. The method of claim 3 further comprising applying a mattifying formulation to the surface before the step of allowing the cosmetic formation to be dispersed.

5. The method of claim 3 further comprising applying a moisturizing formulation to the surface before the step of allowing the cosmetic formation to be dispersed.

6. The method of claim 3 further comprising moving the airbrush in flowing, circular motions at a distance of about four to eight inches from the surface so as to allow a sheer and uniform layer of the cosmetic formulation to be applied onto the surface.

7. The method of claim 3 further comprising the steps of introducing a shimmer formulation into the gravity feed cup, allowing the shimmer formulation to be aspirated into the airbrush, and allowing the shimmer formulation to be dispersed in a directed atomized spray out the air outlet port onto a surface.

* * * * *